(12) United States Patent
Van Ess

(10) Patent No.: US 7,092,750 B2
(45) Date of Patent: Aug. 15, 2006

(54) ECG SIGNAL DETECTION DEVICE

(75) Inventor: David W. Van Ess, Arlington, WA (US)

(73) Assignee: Medtronic Emergency Response Systems, Inc., Redmond, WA (US)

( * ) Notice: Subject to any disclaimer, the term of this patent is extended or adjusted under 35 U.S.C. 154(b) by 490 days.

(21) Appl. No.: 10/418,329

(22) Filed: Apr. 16, 2003

(65) Prior Publication Data

US 2004/0210148 A1  Oct. 21, 2004

(51) Int. Cl.
A61B 5/0428 (2006.01)

(52) U.S. Cl. ..................................... 600/509

(58) Field of Classification Search ........ 600/508–523, 600/372–394
See application file for complete search history.

(56) References Cited

U.S. PATENT DOCUMENTS

| | | | |
|---|---|---|---|
| 4,353,372 A | 10/1982 | Ayer | |
| 4,365,634 A | 12/1982 | Bare et al. | |
| 4,381,789 A | 5/1983 | Naser et al. | |
| 4,583,551 A | * 4/1986 | Pike | |
| 4,841,966 A | 6/1989 | Hagen et al. | |
| 4,850,356 A | 7/1989 | Heath | |
| 4,955,381 A | 9/1990 | Way et al. | |
| 5,080,099 A | 1/1992 | Way et al. | |
| 5,113,869 A | 5/1992 | Nappholz et al. | |
| 5,184,620 A | 2/1993 | Cudahy et al. | |
| 5,235,977 A | 8/1993 | Hirschberg et al. | |
| 5,241,960 A | 9/1993 | Anderson et al. | |
| 5,309,918 A | 5/1994 | Schraag | |
| 5,342,400 A | 8/1994 | Hirschberg et al. | |
| 5,466,244 A | 11/1995 | Morgan | |
| 5,584,865 A | 12/1996 | Hirschberg et al. | |
| 5,700,281 A | 12/1997 | Brewer et al. | |
| 5,713,927 A | 2/1998 | Hampele et al. | |

FOREIGN PATENT DOCUMENTS

EP  0 381 480  8/1990

OTHER PUBLICATIONS

International Preliminary Examination Report for corresponding PCT Application Serial No. PCT/US2004/009410 mailed on Mar. 3, 2005 (5 pages).
B. B. Winter and J. G. Webster, "Driven-right-leg circuit design," IEEE Trans. Biomed. Eng., vol. BME-30, No. 1, pp. 62-66, 1983.
Cardiac Science, "PowerHeart CRM Accessories", www.cardiacscience.com, 2001.

* cited by examiner

Primary Examiner—Scott M. Getzow
(74) Attorney, Agent, or Firm—Shumaker & Sieffert, P.A.

(57) ABSTRACT

An ECG signal detection device that includes a differential amplifier input circuit and a driven reference electrode lead is disclosed. More specifically, the ECG signal detection device includes a differential amplifier input circuit and three-electrode leads, two of which terminate at a common patient coupling device such as an electrode pad or a defibrillator paddle. The third electrode lead terminates at a second, separate patient coupling device. Two electrical cords that include the electrode leads extend between the patient coupling devices and the differential amplifier input circuit. One electrical cord includes the two-electrode leads that terminate at the common patient coupling device. One electrode lead and an associated electrode integrated into the common patient coupling device form one of the ECG signal inputs to the differential amplifier and the second electrode lead and an associated electrode also integrated into the common patient coupling device form a driven reference input to the differential amplifier. The other electrode cord incorporates the third electrode lead. The third electrode lead and an associated electrode integrated into the second, separate patient coupling device form the other ECG signal input to the differential amplifier.

10 Claims, 3 Drawing Sheets

ECG SIGNAL DETECTION DEVICE

FIELD OF THE INVENTION

The present invention relates generally to detecting the electrical activity of a patient's heart and, more particularly, to detecting the electrical activity of a patient's heart using a three-electrode lead electrocardiogram signal device.

BACKGROUND OF THE INVENTION

It is common during medical situations to monitor a patient's heart by sensing the electrical excitation pulses, i.e., the electrocardiogram (ECG) signals, that cause the contraction of the heart's ventricles and atria. ECG signals are commonly detected by an ECG signal detection device that includes a pair of electrodes each incorporated into an adhesive pad designed to be placed on a patient's chest. Leads connect the electrodes to the inputs of a differential input amplifier. The differential amplifier detects the slight ECG signals associated with the contraction of the heart and amplifies the ECG signals so that the ECG signals can be analyzed and/or displayed for analysis by a medical instrument such as a defibrillator. Because the magnitude of the ECG signals are relatively low and because relatively high patient transthoracic impedance makes isolating the ECG signals difficult, the amplification necessary to display ECG signals is relatively high. Relatively high amplification makes the electrode leads of the ECG signal detection device susceptible to outside electrical noise created by sources such as overhead lights or patient capacitance to earth. The outside electrical noise created by nearby power sources (50–60 Hz) can be nullified by a band-pass filter that passes ECG signals over a lower bandwidth (2–40 Hz). Employing a low frequency band-pass filter has the disadvantage of requiring operators to "stand clear" of the patient so as to not affect the reading of the patient being analyzed. Recently, medical instruments have begun analyzing ECG signals using various Shock Advisory System (SAS) algorithms. Such algorithms are incompatible with the low pass filtering of ECG signals because they require signal frequencies above the upper cut-off frequency of the low pass filter passband in order to properly diagnose ECG signals and, thus, a patient's condition. However, as noted above, raising the cut-off frequency of the passband results in greater susceptibility to outside electrical noise. Outside electrical noise can create false ECG signals that could be misinterpreted by an operator or SAS algorithm. Incorrect interpretation of the ECG signals can result in inappropriate treatment.

The effect of outside electrical noise associated with ECG signals can be reduced if not entirely eliminated by applying a third electrode to a patient's chest and connecting the third electrode to a driven reference input of the differential input amplifier via a suitable driven reference lead circuit. The capability of a differential input amplifier to eliminate the effect of outside electrical noise is expressed in decibels as a common mode rejection ratio (CMRR). As a differential amplifier's CMRR becomes larger, it is less susceptible to outside electrical noise, i.e., more outside electrical noise detected by the electrode leads is rejected.

As stated above, two of the electrode leads of a typical three-electrode lead differential amplifier input system form signal detection electrode leads. The third electrode lead functions as a driven reference electrode lead. The third electrode lead provides a low-resistance path for grounding outside electrical noise signals, significantly reducing the effect of outside electrical noise on ECG signals. When a third electrode lead is used as a driven reference, the CMRR of a typical differential input amplifier is increased by approximately 30 dB.

As a result, many ECG signal devices include a third electrode and a third electrode lead for use as a driven reference for the differential amplifier receiving the ECG signals. In the past, the three-electrode leads have been separate and were attached to the patient's chest using three separate adhesive pads each housing an electrode. That is, the patient end of each electrode lead is attached to an electrode mounted in a separate adhesive pad. Most such adhesive pads are disposable, i.e., only intended for use with one patient.

The application of three separate electrode pads to a patient is disadvantageous in emergency situations. It is inconvenient to fix a third electrode pad to a patient when time is critical. Additionally, when a defibrillator unit is being used for both ventricular defibrillation and ECG signal monitoring, fixing a third electrode pad to a patient while holding two defibrillator pads or paddles, each of which also functions as an ECG signal detection electrode for an ECG signal device, is difficult at best. Even though a third or reference electrode lead reduces the possibility of ECG signal error, it has been found that the practice of applying a separate reference electrode lead to a patient is too inconvenient to be acceptable during emergency situations.

Thus, there exists a need for methods and apparatus that overcome these disadvantages. The present invention is directed to providing such methods and apparatus.

SUMMARY OF THE INVENTION

In accordance with the present invention, an ECG signal detection device for detecting a patient's ECG signals that includes a differential amplifier input circuit and a driven reference electrode lead is provided. More specifically, the ECG signal detection device includes a differential amplifier input circuit and three-electrode leads, two of which terminate at a common patient coupling device such as an adhesive electrode pad or defibrillator paddle. The third electrode lead terminates at a second, separate patient coupling device. Two electrical cords that include the electrode leads extend between the patient coupling devices and the differential amplifier input circuit, also called a front end circuit. One electrical cord includes the two-electrode leads that terminate at the common patient coupling device. One electrode lead connects an associated electrode integrated into the common patient coupling device to one of the ECG signal inputs of the differential input amplifier and the second electrode lead connects an associated electrode also integrated into the common patient coupling device to the driven reference input of this differential amplifier. The other electrode cord incorporates the third electrode lead. The third electrode lead connects an associated electrode integrated into the second, separate patient coupling device to the other ECG signal input of the differential input amplifier.

Including the driven reference electrode in a patient coupling device that also includes one of the signal electrodes and incorporating the leads to both electrodes in a common electrical cord eliminates the inconvenience and disadvantages associated with a separate patient coupling device and a separate electrical cord for the driven reference input to the differential amplifier.

In accordance with alternate aspects of this invention, the ECG signal detection device includes four electrode leads, two of which terminate at one common patient coupling device and two of which terminate at a second common patient coupling device. Each of two cords includes two-electrode leads, one of which is a signal lead and the other of which is a driven reference lead.

In accordance with further aspects of this invention, the patient coupling devices are disposable defibrillator electrode pads.

In accordance with alternate aspects of this invention, the patient coupling devices are defibrillator hard paddles.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
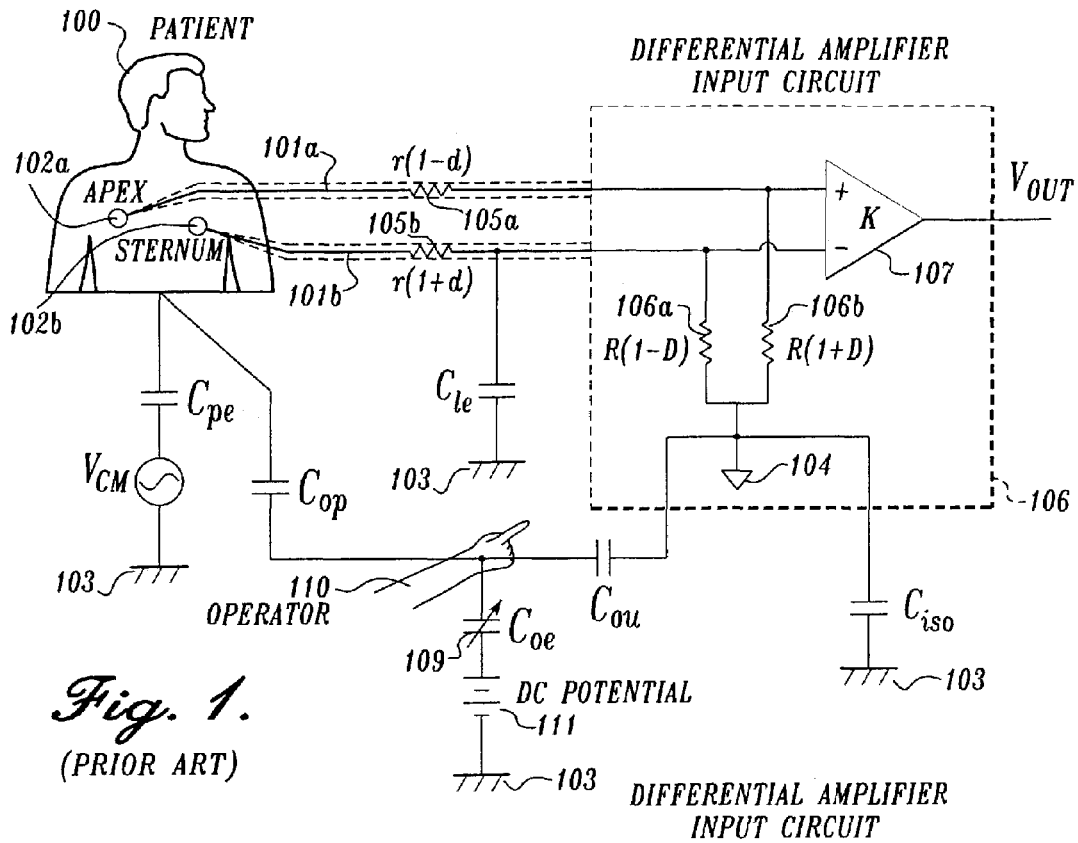
FIG. 1 is a circuit diagram depicting a typical prior art two-electrode ECG signal detection device.

FIG. 1 illustrates a typical prior art two-electrode electrocardiogram (ECG) signal detection device suitable for use in a medical instrument such as a defibrillator. The illustrated two-electrode ECG signal detection device includes a differential amplifier input circuit 106, diagrammatically represented by a differential amplifier 107, and two-electrode leads 101a and 101b that are electrically connected to the electrodes of separate patient coupling devices 102a and 102b suitable for placement on the chest of a patient 100. One electrode lead 101a is connected to the positive (+) input of the differential amplifier 107 and the other electrode lead is connected to the negative (−) input of the differential amplifier. The patient coupling devices may be disposable electrode pads that contain an adhesive for attaching the pads to the chest of the patient 100 or standard ("hard") defibrillator paddles. Each of the leads 101a and 101b is housed in a separate cord diagrammatically depicted by dashed lines located on either side of the leads.

One of the two patient coupling devices 102a forms an apex electrode pad and the other patient coupling device 102b forms a sternum electrode pad 102b. The apex electrode pad 102a and sternum electrode pad 102b are not strictly defined as either one is interchangeable with the other.

Each electrode lead 101a and 101b has an associated electrical impedance, represented by r. Inherent to the set of two-electrode leads is a relatively small difference in impedance between the two-electrode leads, represented by d. Thus, the impedance 105a of the electrode lead 101a connected to the apex electrode pad 102a can be represented by r(1−d) and the impedance 105b of the electrode lead 101b connected to the sternum electrode pad 102b can be represented by r(1+d).

In addition to the impedance of the electrode leads, each electrode lead has an associated impedance 106a, 106b between the electrode lead and system ground 104. This impedance is referred to as the input impedance of the differential amplifier input circuit 106 and is generally represented by R. Again, there will be small difference between the two impedances, which can be represented by D. Thus, the impedance between the electrode lead connected to the apex electrode pad and system ground can be represented by R(1+D) and the impedance between the electrode lead connected to the sternum electrode pad and system ground can be represented by R(1−D).

An ideal ECG signal detection device would have infinite input impedance, zero electrode lead impedance and be infinitely isolated from its surroundings. Real systems, however, have a finite differential amplifier input impedance R and finite electrode lead impedance r. Real systems also are electrically coupled to outside electrical noise and magnetic fields existing in the surrounding environment. Such outside electrical noise couplings are represented by capacitances in FIG. 1. The capacitances include a capacitance between the electrode leads 101a and 101b and earth 103, represented by $C_{le}$ and a capacitance between system ground 104 and earth 103, represented by $C_{iso}$. The capacitances also include a capacitance between system ground 104 and an operator 110, represented by $C_{ou}$, and a capacitance between the patient 100 and the operator 110, represented by $C_{op}$. The capacitances further include a variable capacitance between the operator 110 and earth 103, represented by $C_{oe}$. The latter capacitance (i.e., $C_{oe}$) has an associated DC potential 111. Finally, the capacitances include a capacitance between the patient 110 and earth 103, represented by $C_{pe}$, which has an associated common mode voltage, represented by $V_{CM}$.

Because of the difference in electrode lead impedance, outside electrical noise picked up by the various capacitances identified above will cause a current to flow in the electrode leads 101a and 101b connected to the inputs of the differential amplifier input circuit 106. This current, called a common mode current, will have a small effect on the actual ECG signals carried by the electrode leads 101a and 101b. Common mode current can create ECG signal errors that can lead to incorrect patient diagnosis.

The capability of a differential amplifier input circuit to eliminate the effect of outside electrical noise is defined by a common mode rejection ratio (CMRR) expressed in decibels. As the CMRR of a differential amplifier input circuit becomes greater, the circuit is less susceptible to outside electrical noise. The CMRR of a typical two-electrode lead differential amplifier input circuit of the type depicted in FIG. 1 can be expressed by the following equation.

$$CMRR = [2 * s * C_{iso} * r * (d+D)] + [R/2 * K * s * C_{iso}] \qquad (1)$$

where:

r = any series impedance between the patient and the differential amplifier input circuit, i.e., the impedance of the electrode leads;

d = the mismatch between the series impedance of the electrode leads;

R = any impedance between the electrode leads and system ground;

D = the mismatch between the electrode lead and system ground impedances;

$C_{iso}$ = the capacitance between earth and system ground;

K = the CMRR of the differential input amplifier connected to the electrode leads; and s = the common mode frequency.

As will be readily apparent to those skilled in the art, in order to increase the CMRR it is necessary to either reduce the capacitance to earth ($C_{iso}$), reduce the electrode lead impedance (r), reduce the mismatch values d and D, or reduce the value of d+D.

Figure 1A:
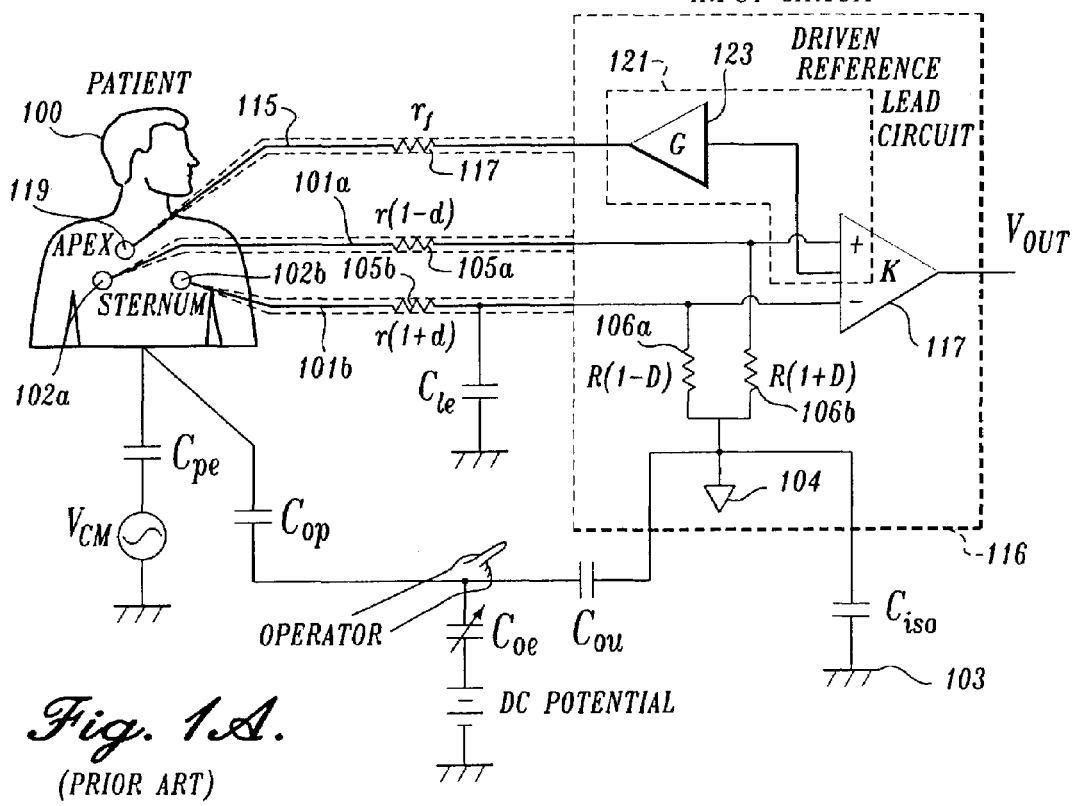
FIG. 1A is a circuit diagram depicting a typical prior art three-electrode ECG signal detection device.

Another option for reducing the CMRR is to use a somewhat different electrical circuit architecture, specifically a prior art architecture of the type illustrated in FIG. 1A that incorporates a third electrode lead 115 that provides a driven reference to the differential amplifier input circuit 116, diagrammatically represented by differential amplifier 117 having a reference input. The third or driven reference electrode lead 115 provides a low-resistance path for common mode current, resulting in a majority of the common mode current flowing through the driven reference electrode lead 115 rather than the signal electrode leads 101a and 101b. The end result is that common mode current present at the signal inputs, i.e., the positive (+) and negative (−) inputs, of the differential amplifier input circuit 117 is significantly reduced.

One end of the driver reference electrode lead 115 shown in FIG. 1A is connected to the electrode of a patient coupling device 119 positioned on the chest of the patient 100. Preferably, the patient coupling device 119 is a disposable pad suitable for adhesive attachment to the chest of the patient 100. The driven reference electrode lead 115 has an associated impedance 117 represented by $r_f$. Preferably, the driven reference electrode pad 119 is located near either the apex electrode pad 102a (shown) or the sternum electrode pad 102b or equidistant from both the apex electrode pad 102a and the sternum electrode pad 102b of the patient 100. The other end of the driven reference electrode lead 115 is connected to the driven reference input of the differential input amplifier circuit 107 via a conventional driven reference lead circuit 121. The driven reference electrode lead circuit 121 is depicted diagrammatically in FIG. 1A as a single amplifier 123 having a gain G, even though in practice the circuit is more complex.

The series impedance, $r_f$, of the driven reference electrode lead 115 is 1−G times smaller than it would be if the driven reference input of the differential amplifier input circuit is connected to system ground, as it would be if employed in a circuit of the type shown in FIG. 1. The gain G of the amplifier 123 is optimally configured to provide a low-resistance path for common mode current that is created by outside electrical noise. The proper configuration optimally reduces the common mode gain of the ECG detection device. Since adding a driven reference electrode lead circuit to a differential amplifier included in an ECG detection device is well known, FIG. 1A is not described further here except to note that the CMRR of such an ECG signal device can be expressed by the following equation:

$$CMRR = [2*s*C_{iso}*r_f/(1-G)*(2d+2D)*r/R] \quad (2)$$

where:

S, $C_{iso}$, d, D, R and r are as described above; and $r_t$ is the series impedance of the driven reference electrode lead and G is the gain of the driven reference electrode lead amplifier.

In the past, as shown pictorially by the dashed lines surrounding them, the three-electrode leads, i.e., the apex electrode lead 110a, the sternum electrode lead 101b and the driven reference electrode lead 115, of a typical three-electrode lead ECG signal detection device have been included in separate electrical cords extending to their associated electrode pads 102a, 102b and 119. In a routine situation requiring ECG signal diagnostics, sufficient time exists for an operator to apply all three electrode pads to a patient's chest. In recent years, non-routine or emergency defibrillation situation protocols requiring ECG signal diagnostics prior to defibrillation have been developed. In an emergency situation, operators sometimes choose not to attach the third (driven reference) electrode pad to a patient because such attachment is not absolutely necessary to the detection of a patient's ECG signals. More specifically, since time is critical in emergency situations, first care providers sometimes do not bother to attach the driven reference electrode pad. Furthermore, when a first care provider is using a defibrillator employing two shock delivery (hard) paddles, it may be impractical for an operator to fix a driven reference electrode pad to a patient's chest in order to use the defibrillator paddles to provide an ECG signal for diagnostic purposes. The present invention is directed to avoiding these disadvantages.

As will be better understood from the following description of the presently preferred embodiments of this invention, the present invention provides an ECG signal detection device for monitoring the electrical activity of a human heart that includes a differential amplifier input circuit, a driven reference electrode lead-circuit and at least three-electrode leads. However, rather than each of the electrode leads included in separate cords or cables extending between electrode pads and the differential amplifier input circuit, two of the three-electrode leads reside or are included within the same electrical cord. Further, the electrodes that electrically couple the two-electrode leads to a patient's chest are contained in a common pad or paddle housing. Including two-electrode leads into a single electrical cord and including two electrodes in a common structure eliminates the need to affix a third electrode pad to a patient in an emergency situation.

Figure 2:
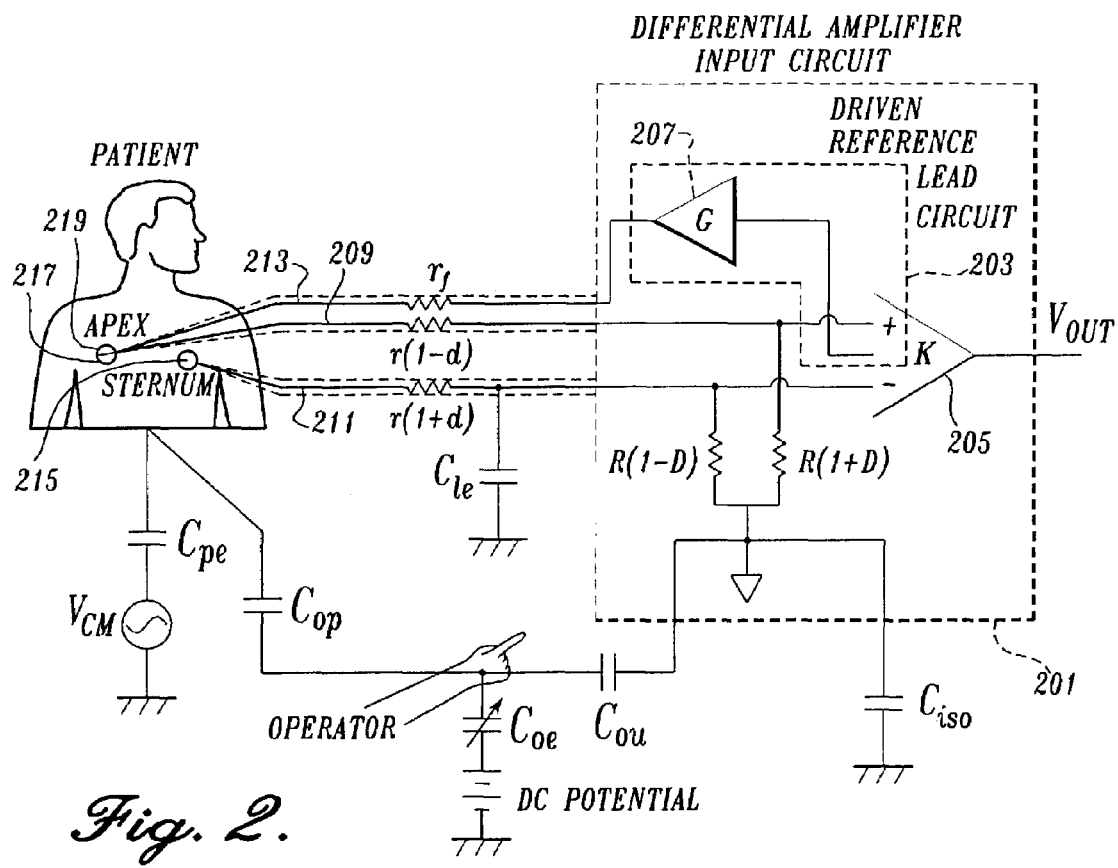
FIG. 2 is a circuit diagram of a three-electrode ECG signal detection device formed in accordance with the present invention.

FIG. 2 illustrates a three-electrode lead ECG signal detection device formed in accordance with the invention. Like the three-electrode lead ECG signal detection device illustrated in FIG. 1A, the three-electrode lead ECD signal detection device illustrated in FIG. 2 includes a differential amplifier input circuit 201 and a driven reference lead circuit 203. The differential amplifier input circuit 201 is diagrammatically illustrated as formed by a differential amplifier 205 having a reference lead input as well as two signal outputs. Also like FIG. 1A, the driven reference lead circuit 203 is diagrammatically illustrated as comprising a single amplifier 207 having a gain G. The reference lead input of the differential amplifier 205 is connected to the input of the amplifier 207 and the output of the amplifier 207 is connected to a driver reference electrode lead 213.

In addition to the differential amplifier input circuit 201 and the driven reference lead circuit 203, the three-electrode lead ECG signal detection device illustrated in FIG. 2 includes an apex electrode lead 209, a sternum electrode lead 211 and the driven reference electrode lead 213. Also like FIG. 1A, the sternum electrode lead 211 is included in a cord diagrammatically illustrated by dash lines located on opposite sides of the sternum electrode lead 211. However, rather than the apex electrode lead 209 and the driven reference electrode lead 213 being included in separate cords, the apex electrode lead 209 and the driven reference electrode lead 213 are included in a common cable or cord, as diagrammatically shown by the dash lines located above the driven reference electrode lead 213 and below the apex driven lead 209.

Figure 4:
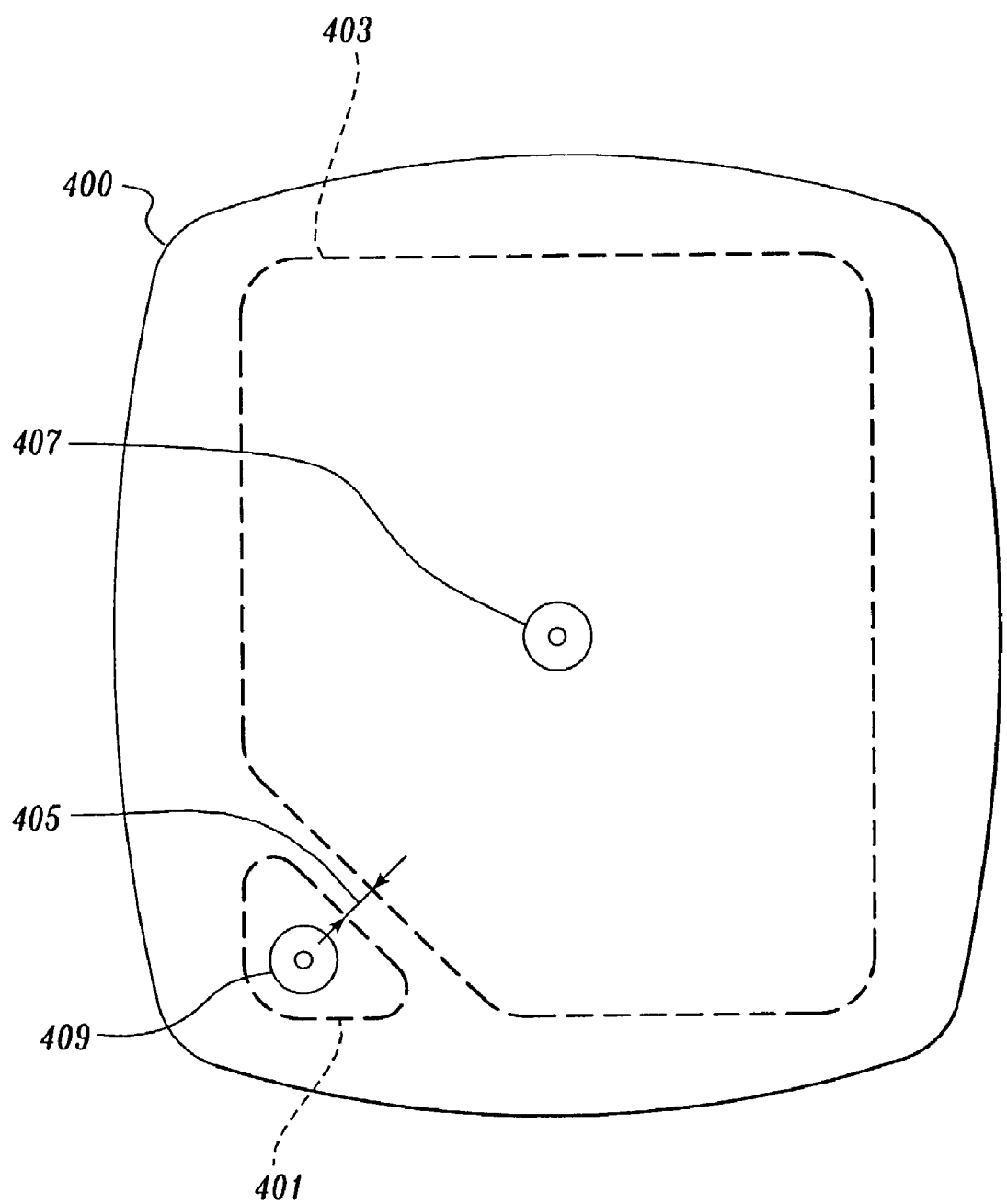
FIG. 4 is a plan view of a disposable electrode pad formed in accordance with the present invention.

Also as in FIG. 1A, the sternum electrode lead 211 terminates at a sternum electrode pad 215. However, unlike FIG. 1A, while the apex electrode lead 209 and the driven reference electrode lead 213 terminate at an apex electrode pad 217 and a driven reference electrode pad 219, the pads are common, i.e., the electrodes are integrated into a common patient coupling device, rather than being separate. That is, while the apex electrode and the driven reference remain separate, as shown in FIG. 4 and described below, they are housed in a common pad. For purposes of illustration only, the separate electrode, common pad arrangement is diagrammatically shown in FIG. 2 by a line splitting the common pad that houses the apex electrode pad 217 and the driven reference electrode pad.

As an alternative to the driven reference electrode lead 213 being located in the same cord as the apex electrode lead 209 and the driven reference electrode pad 219 being housed in a pad that is common with the apex electrode pad 217, the driven reference electrode lead could be located in the same cord as the sternum electrode lead 211 and the driven reference electrode pad 219 could be housed in a pad that is common with the sternum electrode pad 215. Or, as shown in FIG. 3 and described next, both arrangements can be employed in a four-electrode lead ECG signal detection device formed in accordance with the invention.

Figure 3:
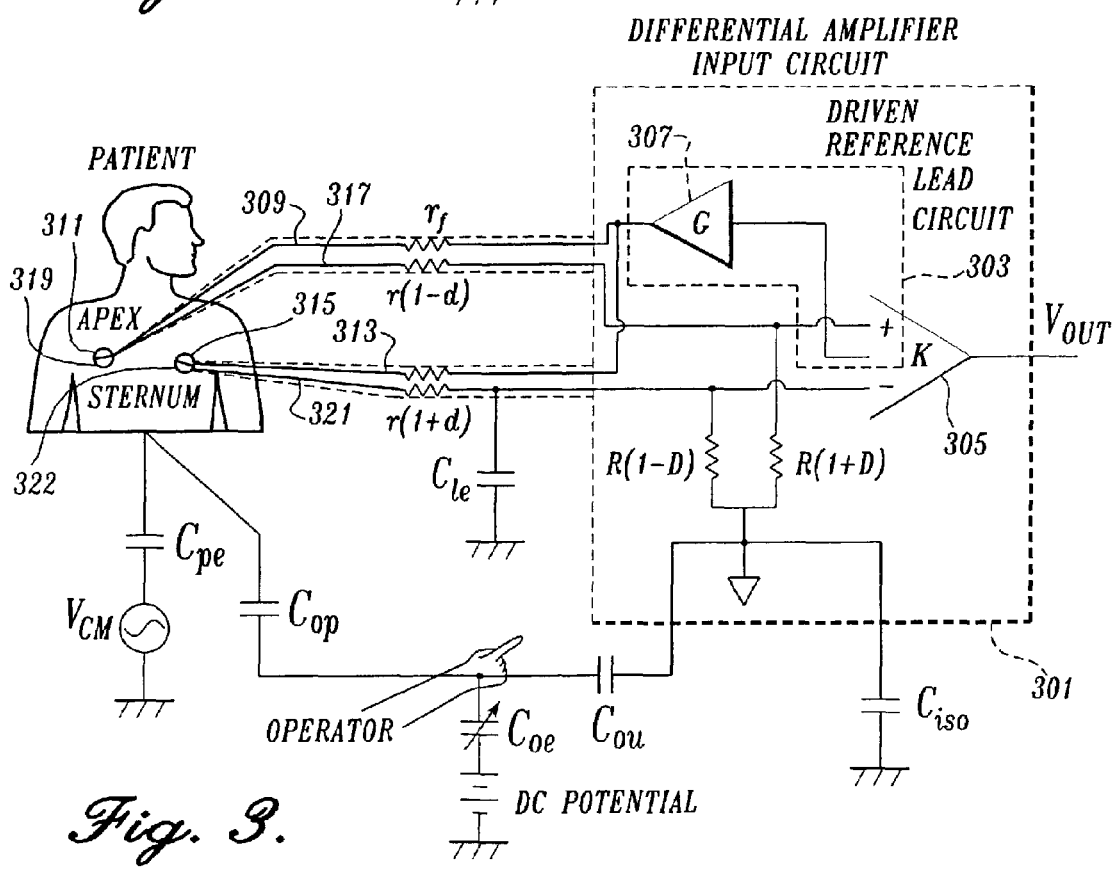
FIG. 3 is a circuit diagram of a four-electrode ECG signal detection device formed in accordance with the present invention.

As with FIGS. 1A and 2, the ECG signal detection device shown in FIG. 3 includes a differential amplifier input circuit 301 and a driven reference lead circuit 303. The differential amplifier input signal 301 is diagrammatically illustrated as formed by a differential amplifier 305 having a reference input and two signal inputs. The driven reference lead circuit 303 is diagrammatically illustrated as formed by a single amplifier 307 having a gain G. The input of the amplifier 307 is connected to the reference lead input of the differential amplifier 305. The output of the amplifier 307 is connected through a first driven reference electrode lead 309 to a first driven reference electrode pad 311. The output of the amplifier 307 is also connected through a second driven reference electrode lead 313 to a second driven reference electrode 315. As with FIGS. 1A and 2, one of the signal inputs of the differential amplifier is connected through an apex electrode lead 317 to an apex electrode pad 319. The other signal input of the differential amplifier 305 is connected through a sternum electrode lead 321 to a sternum electrode pad 323.

The first driven reference electrode pad 311 and the apex electrode pad are combined in a common pad as are the second driven reference electrode pad 315 and the sternum electrode pad 322. A suitable common pad is illustrated in FIG. 4 and described below. Further, the first driven reference electrode lead 309 and the apex electrode lead 317 are included in a common cord or cable as represented by the dash lines located above the driven reference electrode lead 309 and below the apex electrode lead 317. Likewise the second driven reference electrode lead 313 and the sternum electrode lead 321 are included in a common cord or cable as represented by the dash line above the second driven reference electrode lead 313 and below the sternum reference electrode lead 321. Thus, while the ECG signal device illustrated in FIG. 3 includes two driven reference electrode leads as well as an apex and sternum electrode leads, only two cables or cords are employed, thereby avoiding the problems associated with three (or more) separate cables or cords.

FIG. 4 is a top plan view of a common electrode pad 400 suitable for housing a reference electrode 401 and either an apex electrode or a sternum electrode 403. The reference electrode 401 and the apex or sternum electrode 403 are illustrated by dashed lines since their exposed surfaces are located on the remote side of the common electrode pad 400 illustrated in FIG. 4. While the reference electrode 401 and the apex or sternum electrode 403 can take on various shapes, for ease of illustration, the apex or sternum electrode pad is shown as generally rectangular in shape with one corner removed and the reference electrode 401 is located in the corner. The electrodes are spaced apart by a distance 405 sufficient to minimize appreciable capacitance between the electrodes. An apex or sternum connector 407 and a reference electrode connector 409 are also illustrated in FIG. 4. The connectors 407 and 409 may be any suitable detachable connectors well known in the art, or may represent a permanent attachment to the respective electrode leads. As is well known in the art, the common electrode pad 400 includes an electrically conducting adhesive on the electrode side of the pad. As will be readily appreciated by those skilled in the art and others, in addition to forming signal electrodes for the ECG signal detection device described herein, the apex and sternum electrodes can also function as defibrillation electrodes.

While FIG. 4 illustrates an electrode pad 400, commonly referred to as a soft electrode suitable for adhesive attachment to the chest of the patient, as will be readily appreciate by those skilled in the art and others, a similar electrode configuration can be created in a "hard" paddle of the type commonly associated with external defibrillators. However, as with the common electrode pad illustrated in FIG. 4, in accordance with this invention, the leads running to the reference electrode 401 and the apex or sternum electrode 403 are housed in a common cord or cable. Consequently, while the presently preferred embodiment of the invention has been illustrated and described, it will be appreciated that various changes can be made without departing from the spirit and scope of the invention as defined by the appended claims.

The embodiments of the invention in which an exclusive property or privilege is claimed are defined as follows:

1. An electrocardiogram (ECG) signal detection device comprising:
   a differential amplifier circuit having signal inputs and a driven reference input;
   a driven reference circuit connected to the driven reference input of said differential amplifier circuit;
   at least one signal electrode lead connected to a signal input of said differential input amplifier circuit;
   a driven reference electrode lead connected to said driven reference circuit, said driven reference electrode lead and said at least one signal lead included in a common cable; and
   a patient coupling device, said patient coupling device including a signal electrode and a driven reference electrode contained in a common housing, said signal electrode connected to said at least one signal electrode lead and said driven reference electrode connected to said driven reference electrode lead.

2. The electrocardiogram signal detection device as claimed in claim 1, wherein said patient coupling device is an electrode pad.

3. The electrocardiogram signal detection device as claimed in claim 2, wherein said electrode pad is an adhesively attachable pad.

4. The electrocardiogram signal detection device as claimed in claim 3, wherein said adhesively attachable pad is disposable.

5. The electrocardiogram signal detection device as claimed in claim 1, wherein said patient coupling device is a hard paddle.

6. The electrocardiogram signal detection device as claimed in claim 1, further comprising:
- a second signal electrode lead connected to a signal input of said differential amplifier circuit; a second driven reference electrode lead connected to said driver reference circuit, said second signal electrode lead and said second driven reference electrode lead contained in a second common cable; and
- a second patient coupling device, said second patient coupling device including a signal electrode and a driven reference electrode contained in a common housing, said signal electrode connected to said second signal electrode lead and said driven reference electrode connected to said driven reference electrode lead.

7. The electrocardiogram signal detection device as claimed in claim 6, wherein said patient coupling devices are electrode pads.

8. The electrocardiogram signal detection device as claimed in claim 7, wherein said electrode pads are adhesively attachable pads.

9. The electrocardiogram signal detection device as claimed in claim 8, wherein said adhesively attachable pads are disposable.

10. The electrocardiogram signal detection device as claimed in claim 6, wherein said patient coupling devices are hard paddles.

* * * * *